United States Patent [19]

Kimura et al.

[11] 4,207,159
[45] Jun. 10, 1980

[54] APPARATUS FOR MEASUREMENT OF OXYGEN CONCENTRATION

[75] Inventors: Shinji Kimura, Yokohama; Hiroshi Takao, Kamakura; Shigeo Ishitani, Yokosuka; Kenji Ikezawa; Koki Sone, both of Yokohama, all of Japan

[73] Assignee: Nissan Motor Company, Limited, Yokohama, Japan

[21] Appl. No.: 12,763

[22] Filed: Feb. 16, 1979

[30] Foreign Application Priority Data

Jun. 16, 1978 [JP] Japan ................... 53-72044

[51] Int. Cl.² ............................................. G01N 27/58
[52] U.S. Cl. ................................................. 204/195 S
[58] Field of Search ............................ 204/195 S, 1 S; 123/119 E, 119 EC; 60/276; 324/29; 422/98

[56] References Cited

U.S. PATENT DOCUMENTS

| | | | |
|---|---|---|---|
| 3,691,023 | 9/1972 | Ruka et al. | 204/1 T |
| 4,021,326 | 5/1977 | Pollner et al. | 204/195 S |
| 4,045,319 | 8/1977 | Deportes et al. | 204/195 S |
| 4,107,019 | 8/1978 | Takao et al. | 204/195 S |
| 4,126,532 | 11/1978 | Takao et al. | 204/195 S |
| 4,134,818 | 1/1979 | Pebler et al. | 204/195 S |

Primary Examiner—G. L. Kaplan
Attorney, Agent, or Firm—Schwartz, Jeffery, Schwaab, Mack, Blumenthal & Koch

[57] ABSTRACT

An apparatus comprising a probe having an oxygen ion conductive solid electrolyte layer, a potentiometer and a DC power source connected to the probe. The probe comprises a porous and electronically conductive reference electrode layer on one side of the solid electrolyte layer, a similar measurement electrode layer on the other side of the electrolyte layer and a separation layer of an inactive material on the outer side of the reference electrode layer. The separation layer or the solid electrolyte layer, or both, has a porous structure and is formed such that the reference electrode communicates with an exterior atmosphere only through this porous structure, while either the separation layer or the electrolyte layer serves as a substrate of the probe. During measurement, the DC power source keeps a current flowing through the electrolyte layer between the two electrode layers to maintain a reference oxygen partial pressure at the interface between the electrolyte layer and the reference electrode layer.

11 Claims, 12 Drawing Figures

APPARATUS FOR MEASUREMENT OF OXYGEN CONCENTRATION

BACKGROUND OF THE INVENTION

This invention relates to an apparatus for measuring the concentration of oxygen in a fluid, the apparatus being of the type having a layer of an oxygen ion conductive solid electrolyte.

It has been popularized to detect the oxygen content in the exhaust gas from an automotive internal combustion engine as the basis for the control of the air-to-fuel ratio of a combustible mixture fed to the engine by the use of an oxygen sensor that produces an electrical signal representing the detected oxygen content. For such purpose, usually use is made of an oxygen sensor that operates on the principle of a concentration cell and has a layer of a solid electrolyte having a high oxygen ion mobility, e.g. zirconia stabilized with calcia, and two porous and electronically conductive electrode layers of platinum, by way of example, formed respectively on both sides of the solid electrolyte layer. When one side of the solid electrolyte layer in this sensor is exposed (through one of the electrode layers) to a sample gas having an unknown oxygen partial pressure Po and the other side to a reference gas such as air whose oxygen partial pressure Po' is known and there is a difference between the oxygen partial pressures Po and Po', the sensor develops an electromotive force E across the two electrode layers. This electromotive force E is related to the oxygen partial pressures Po and Po' by the Nernst equation:

$$E = \frac{RT}{4F} \ln \frac{Po'}{Po} \qquad (1)$$

where R is the gas constant, T represents the absolute temperature, and F is the Faraday constant. Accordingly the oxygen content in the sample gas can be detected by measuring the electromotive force E with a potentiometer connected to the two electrode layers of the sensor while the total pressure of the sample gas is kept constant.

Conventional oxygen sensors of this type are designed in various ways. As the most popular example, the solid electrolyte layer takes the form of a tube closed at one end so that air used as a reference gas can be introduced into the interior of the tube while the outside of the tube is exposed to a sample gas. The solid electrolyte tube is produced by a sintering technique and has a wall thickness large enough to serve as a structurally basic member of the sensor. However, this oxygen sensor has disadvantages such as unsatisfactory temperature dependence of its output characteristic originating from a large heat capacity and high electrical resistance of the voluminous solid electrolyte tube, insufficiency of the mechanical strength and heat resistance of the solid electrolyte tube and considerably high production cost. When the size of the solid electrolyte tube is reduced to diminish these disadvantages, it becomes necessary to continuously supply a fresh reference gas to the interior of the solid electrolyte tube during measurement, and there arises a problem that the oxygen partial pressure in the electrode layer on the inside of the solid electrolyte tube tends to deviate from the real oxygen partial pressure of the reference gas since a diffusion layer is formed at the surface of this electrode layer by an electrode reaction of the reference gas, resulting in the fact that the oxygen content in the sample gas can no longer be measured accurately. To succeed in accurate measurement of the oxygen content in a sample gas, the solid electrolyte tube in this type of oxygen sensors must provide an interior space large enough in volume to allow continuous replenishment of the reference gas in order that an oxygen concentration gradient created in the vicinity of the inner electrode layer by diffusion of the reference gas is kept as small as possible. It is impractical, therefore, to employ a very small-sized solid electrolyte tube in this type of oxygen sensors.

As a variation of the above described type of oxygen sensors, it has been proposed to confine a volume of reference gas in a closed space in which is disposed one of the electrodes of the concentration cell. However, another disadvantage arises by this modification. During use of this sensor, the oxygen partial pressure of the reference gas confined in the closed space varies as the oxygen in the reference gas is consumed gradually by electrolysis. When the reference oxygen partial pressure is lowered beyond a certain level, it becomes necessary to replenish the closed space with oxygen gas by suspending the measurement and applying a voltage to the solid electrolyte of the sensor with its outer electrode layer (measurement electrode) exposed to another reference gas such as atmospheric air until the sensor resumes the ability of generating a standard level of electromotive force. This sensor, therefore, is unsuitable for continuous and longterm measurement of oxygen concentration in an exterior atmosphere. If it is wished to use this oxygen sensor continuously for a long period of time, the volume of the closed space must be large enough to confine such a large quantity of reference gas that the oxygen partial pressure in the closed space does not exhibit a significant change during use of the sensor. When this requirement is met, the sensor necessarily becomes very large in total size. As an additional disadvantage, this oxygen sensor is rather inferior in its accuracy of measurement because the reference gas confined in the closed space scarcely flows in this space and hence a considerably thick layer of stagnant reference gas is produced along the surface of the inner (reference) electrode layer. Besides, this oxygen sensor is complicated in structure, inconvenient to mass-production and unsatisfactory in mechanical strength and heat resistance.

The disadvantages of the above described oxygen sensors originate primarily from the use of a gas as the source of a reference oxygen partial pressure. Accordingly it has been proposed to utilize a metal-metal oxide system, which exhibits a sort of buffer function derived from a thermodynamic equilibrium, as the source of reference oxygen partial pressure for the concentration cell type oxygen sensor. Such a metal-metal oxide system, e.g. Ni—NiO system, can be formed into a porous layer which is included in the oxygen sensor. Then, a small-sized oxygen sensor can be produced by the employment of thin film and/or thick film techniques. For example, an oxygen sensor of this type comprises a substrate such as of an alumina plate, a reference electrode film deposited on the substrate, a metal-metal oxide film on this electrode, a solid electrolyte film on the metal-metal oxide film and a measurement electrode film on the outside of the solid electrolyte film. This oxygen sensor has many advantages but also has the following disadvantages. When this oxygen sensor is used in a high temperature atmosphere having a relatively high oxygen partial pressure, the reference oxygen partial pressure developed by the metal-metal oxide reference system tends to vary, with the result that the output of the sensor varies with the lapse of time, because of the oxidation of the metal in contact with the solid electrolyte and/or the influence of the exterior gas atmosphere on the reference system. This means that this oxygen sensor does not have a satisfactorily long service life. Besides, this oxygen sensor suffers a considerably high production cost since it is not easy to form a thin layer of a metal-metal oxide system (e.g. by sputtering, electro-deposition or vacuum evaporation) with the maintenance of the most desirable mole ratio (about 1:1) of the metal to the metal oxide.

SUMMARY OF THE INVENTION

It is a general object of the present invention to obviate the above described disadvantages of conventional oxygen sensors of the concentration cell type having a solid electrolyte layer.

It is another object of the invention to provide an apparatus for measurement of oxygen concentration in a fluid, which apparatus comprises a solid electrolyte layer similarly to the above described conventional oxygen sensors but is advantageous in that it can serve for continuous and longterm measurement without exhibiting lowering of its output level, that it exhibits a good response to a change in the oxygen content in a sample fluid, that it is high in accuracy of measurement, that it has a long service life and that it can be made small in size and can be fabricated easily.

An oxygen concentration measurement apparatus according to the invention comprises a probe including a layer of an oxygen ion conductive solid electrolyte, a meter connected to the probe to measure an electromotive force generated by the probe and a DC power source connected to the probe to continuously apply a DC voltage across the solid electrolyte layer in the probe. The probe further comprises a porous and electronically conductive reference electrode layer formed on one side of the solid electrolyte layer, a porous and electronically conductive measurement electrode layer formed on the other side of the solid electrolyte layer and a separation layer of an electrochemically inactive material formed on the outer side of the reference electrode layer. At least one of the solid electrolyte layer and the separation layer has a porous structure permeable to fluids and is formed such that the reference electrode layer communicates with an exterior atmosphere only through this porous structure, and either the solid electrolyte layer or the separation layer is so shaped and sized as to serve as a structurally basic member of the probe. The meter and the DC power source are both connected to the reference and measurement electrode layers of the probe.

Measurement of the oxygen concentration in a fluid by this apparatus is accomplished by disposing the probe entirely in the fluid, continuously applying a DC voltage to the reference and measurement electrode layers to cause a DC current to continuously flow through the solid electrolyte layer and measuring a potential difference between the reference and measurement electrode layers of the probe. The application of a DC voltage to the probe during measurement causes generation of oxygen gas at the interface between the solid electrolyte layer and one of the reference and measurement electrode layers and ionization of oxygen at the interface between the solid electrolyte and the other of the two electrode layers, while the solid electrolyte layer allows oxygen ions to migrate therethrough. As a consequence, a reference oxygen partial pressure can be maintained at the interface between the solid electrolyte and the reference electrode layer without using any reference material comprising oxygen.

The solid electrolyte layer and the two electrode layers are respectively made of materials used in conventional oxygen sensors of the solid electrolyte concentration cell type. The separation layer is usually made of a ceramic material but may alternatively be made of a metal. Preferably, the DC power source is a constant current DC power supply. Optionally, the probe may comprise a heating resistor embedded in the structurally basic member of the probe.

BRIEF DESCRIPTION OF THE DRAWINGS

FIGS. 8-(*a*) to 8-(*c*) illustrate a method of producing a probe portion of a measurement apparatus fundamentally of the construction of FIG. 4;

DESCRIPTION OF THE PREFERRED EMBODIMENTS

Figure 1:
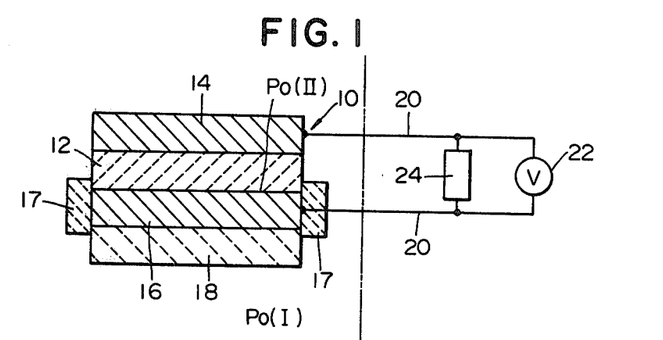
FIG. 1 shows schematically and sectionally a fundamental construction of an oxygen concentration measurement apparatus according to the invention.

Referring to FIG. 1, an oxygen concentration measurement apparatus according to the invention is essentially made up of a probe 10 comprising a layer 12 of an oxygen ion conductive solid electrolyte, a potentiometer 22 or an equivalent means for measuring an EMF the probe generates, leads 20 connecting the meter 22 to the probe 10 and a DC power source 24 connected in parallel with the meter 22 to cause a DC current to flow from one side of the solid electrolyte layer 12 to the other side. The probe 10 has a measurement electrode layer 14 formed on one side of the solid electrolyte layer 12 and a reference electrode layer 16 formed on the other side of the solid electrolyte layer 12. These two electrode layers 14 and 16 are each made of an electronically conductive material and have a porous or gas permeable structure. The outer side of the reference electrode layer 16 is entirely and intimately covered with a separation layer 18, and side surfaces of the reference electrode layer 16 are entirely coated with a shield layer 17 to avoid direct exposure of this electrode layer 16 to an exterior atmosphere in which the probe 10 is disposed to sense oxygen concentration therein. However, both the separation layer 18 and the shield layer 17 may have a microscopically porous structure, i.e. a gas permeable structure. Either the solid electrolyte layer 12 or the separation layer 18 is so designed as to serve as a structurally basic member of the probe 10, and at least one of the solid electrolyte layer 12 and the separation layer 18 is made to have a porous or gas permeable structure. Thus, a fluid subject to measurement comes into contact with the reference electrode layer 16 through the openings or interstices in the solid electrolyte layer 12 and/or the separation layer 18. It is possible to utilize either the solid electrolyte layer 12 or the separation layer 18 also as the shield layer 17.

The leads 20 are attached to the measurement electrode layer 14 and the reference electrode layer 16 for measurement of an EMF generated by the solid electrolyte layer 12 in dependence on a difference between an oxygen partial pressure Po(I) in the exterior atmosphere and another oxygen partial pressure Po(II) at the interface between the solid electrolyte layer 12 and the reference electrode layer 16 by utilizing the meter 22. These leads 20 connect the DC power source 24, too, to the probe 10 so that either a constant current or a constant voltage may be applied between the two electrode layers 14 and 16. (Switches in the feed circuit (20) are omitted from illustration.)

As will be understood from the illustrated construction, the provision of the DC power source 24 is a feature of an oxygen concentration measurement apparatus according to the invention.

When the probe 10 of FIG. 1 is disposed in an oxygen-containing gas atmosphere without utilizing the DC power supply 24, i.e. without applying externally any voltage between the two electrode layers 14 and 16, and there is a difference between the oxygen partial pressure Po(I) in the gas atmosphere and the oxygen partial pressure Po(II) at the interface between the solid electrolyte layer 12 and the reference electrode layer 16, there occurs migration of oxygen ions from one side of the solid electrolyte layer 12 to the other side in a direction to nullify the difference between Po(I) and Po(II). If Po(I)>Po(II), a reaction represented by $O_2+4e\rightarrow 2O^{2-}$ occurs at the interface between the measurement electrode layer 14 and the solid electrolyte layer 12, so that oxygen ions migrate through the solid electrolyte layer 12 towards the reference electrode layer 16. Accordingly a reaction represented by $2O^{2-}\rightarrow O_2+4e$ occurs at the interface between the solid electrolyte layer 12 and the reference electrode layer 16, so that Po(II) increases gradually until Po(I) becomes equal to Po(II), meaning establishment of an equilibrium state, and hence the electromotive force E becomes zero. If initially Po(I)<Po(II), oxygen molecules present at the interface between the reference electrode layer 16 and the solid electrolyte layer 12 flow into the exterior gas atmosphere until Po(I) becomes equal to Po(II). Thus, in either case the probe 10 stops generating an EMF upon disappearance of a difference between Po(I) and Po(II).

According to the invention, the probe 10 is used with continued application of a DC voltage between the two electronically conductive electrode layers 14 and 16 from the DC power source 24 in order to cause electrolytic generation of reference oxygen gas at the interface between the reference electrode layer 16 and the solid electrolyte layer 12 and also in the pores of the solid electrolyte 12 thereby to maintain a substantially constant level of reference oxygen partial pressure. The apparatus of FIG. 1 functions on the following principle.

Assume that the measurement electrode layer 14 is connected to the negative terminal of the DC power source 24 and the reference electrode layer 16 to the positive terminal. Then there occurs migration of negatively charged oxygen ions in the solid electrolyte layer 12 towards the reference electrode layer 16, resulting in an increase in the oxygen partial pressure at the interface between the solid electrolyte layer 12 and the reference electrode layer 16. In this case, the following reactions occur in the probe 10.

(1) At the interface between the measurement electrode layer 14 and the solid electrolyte layer 12, oxygen in the exterior gas atmosphere subject to measurement is ionized:

$$O_2+4e\rightarrow 2O^{2-}$$

(2) In the solid electrolyte layer 12, the negatively charged oxygen ions ($2O^{2-}$ formed by the above reaction) migrate towards the reference electrode layer 16.

(3) At the interface between the solid electrolyte layer 12 and the reference electrode layer 16, the oxgen ions migrated through the solid electrolyte layer 12 turn into oxygen molecules:

$$2O^{2-}\rightarrow O_2+4e$$

The gaseous oxygen formed by this reaction accumulates at the interface between the solid electrolyte layer 12 and the reference electrode layer 16, so that Po(II) increases.

Aside from these reactions (1), (2) and (3), a portion of the accumulated oxygen gas flows out into the exterior atmosphere through a porous structure of the separation layer 18 (and/or the solid electrolyte layer 12). Therefore, the oxygen partial pressure Po(II) at the interface between the solid electrolyte layer 12 and reference electrode layer 16 becomes nearly constant after the lapse of a short period of time from the start of measurement, so that the measurement of oxygen concentration in the exterior gas atmosphere can be conducted with the maintenance of a nearly constant reference oxygen partial pressure.

When the measurement electrode layer 14 is connected to the positive terminal of the DC power source 24 and the reference electrode layer 16 to the negative terminal, the following reactions occur in the probe 10 in the reverse way to the above explained reactions (1), (2) and (3).

(1') At the interface between the solid electrolyte layer 12 and the reference electrode layer 16, oxygen in the exterior atmosphere is ionized:

$$O_2+4e\rightarrow 2O^{2-}$$

(2') In the solid electrolyte layer 12, the negatively charged oxygen ions ($2O^{2-}$ formed by the above reaction) migrate towards the measurement electrode layer 14.

(3') At the interface between the solid electrolyte layer 12 and the measurement electrode layer 14, the oxygen ions migrated through the solid electrolyte layer 12 turn into oxygen molecules:

$$2O^{2-}\rightarrow O_2+4e$$

Accordingly there occurs a decrease in the oxygen partial pressure Po(II) at the interface between the reference electrode layer 16 and the solid electrolyte layer 12. However, Po(II) becomes nearly constant after a short while because gaseous oxygen flows into the probe 10 and arrives at the interface between the reference electrode layer 16 and the solid electrolyte layer 12 through the porous separation layer 18 (and/or the porous solid electrolyte layer 12). Therefore, it is possible to maintain a substantially constant reference oxygen partial pressure also in this case.

It is clarified that Po(II) can be maintained constant irrespective of the manner of connection of the two electrode layers 14 and 16 to the positive and negative terminals of the DC power source 24. However, when it is desirable that Po(II) takes constantly a relatively large value, it is preferable to connect the reference electrode layer 16 to the positive terminal of the DC power source 24 since in this case oxygen is supplied electrolytically from the measurement electrode layer 14 to the reference electrode layer 16 as replenishment for dissipation of gaseous oxygen into the exterior atmosphere through the porous separation layer 18. On the contrary, when it is desired that Po(II) takes constantly a relatively small value, it is preferable to connect the reference electrode layer 16 to the negative terminal of the DC power source 24 since in this case a portion of gaseous oxygen supplied from the exterior atmosphere to the reference electrode layer 16 is expelled electrolytically from the reference electrode layer 16 towards the measurement electrode layer 14.

In a measurement apparatus according to the invention, a voltage V indicated by the meter 22 does not exactly accord with the electromotive force E originating from a difference between the oxygen partial pressure Po(I) and Po(II) but has a definite relation with this electromotive force E as expressed by the following equation.

$$V = \frac{Er_1 + eR_3}{R_1 + R_3(R_1/R_2 + 1)} \quad (2)$$

wherein, e is the output voltage of the DC power source 24, $R_1$ is the total resistance of the measurement circuit, $R_2$ is the impedance of the meter 22, and $R_3$ is the internal resistance of the probe 10. Since the reference oxygen partial pressure Po(II) in the probe 10 is determined by the intensity of a current flowing between the two electrode layers 14, 16 and the gas diffusion ability of the separation layer 18 and accordingly takes a definite value, the oxygen concentration in an exterior gas atmosphere can be deduced from the indicated voltage V by utilizing Equation (2) as well as Nernst Equation (1). Since the indicated voltage V varies as the oxygen partial pressure Po(I) and hence the electromotive force E vary while V is proportional to E, it is possible to utilize the voltage V as a signal to control, for example, the rate of fuel injection into an internal combustion engine.

The material of the solid electrolyte layer 12 is selected from oxygen ion conductive solid electrolyte systems used for conventional oxygen sensors of the oxygen concentration cell type. Examples are $ZrO_2$ stabilized with CaO, $Y_2O_3$, SrO, MgO, $WO_3$ or $Ta_2O_5$; $Bi_2O_3$ stabilized with $Nb_2O_5$, SrO, $WO_3$ or $Ta_2O_5$; $ThO_2$—$Y_2O_3$ system and CaO—$Y_2O_3$ system. When the solid electrolyte layer 12 is made to be a structurally basic member of the probe 10, this layer 12 takes the form of a sufficiently thick plate obtained by machining a sintered body of a selected oxide system. When the separation layer 18 serves as the structurally basic member or substrate of the probe 10, the solid electrolyte layer 12 may take the form of a thin film deposited on the separation layer 18 by sputtering, vacuum evaporation or an electrochemical process, or by firing of a solid electrolyte paste applied onto the separation layer 18.

The electrode layers 14 and 16 are each made of a material selected from electrode materials for conventional oxygen sensors utilizing a solid electrolyte. Examples are Au, Ag and SiC which do not exhibit any catalytic action on oxidation reactions and catalytic metals such as Ru, Pd, Rh, Os, Ir and Pt, including alloys of these platinum group metals and alloys of a platinum group metal with a base metal. The electrode layers 14 and 16 are formed by sputtering, vacuum evaporation, an electrochemical process or firing of a metal powder paint or paste.

When the solid electrolyte layer 12 serves as a structurally basic member of the probe 10, the separation layer 18 takes the form of a porous coating of either an amorphorous or crystalline inorganic material which may be sintered or fired on the surface of the solid electrolyte layer 12. For example, glass compositions and ceramics are of use.

In the case of the separation layer 18 being a structurally basic member of the probe 10, it is suitable to use an electrically nonconductive inorganic material such as alumina, mullite, spinel, silica or forsterite as the material for the separation layer 18. In this case the separation layer 18 may be made to have either a dense structure impermeable to gases or a somewhat porous structure. Also it is possible to use an electronically conductive inorganic material such as stainless steel, a nickel-base heat-resistant alloy or a cermet as the material of the separation layer 18.

Figure 2:
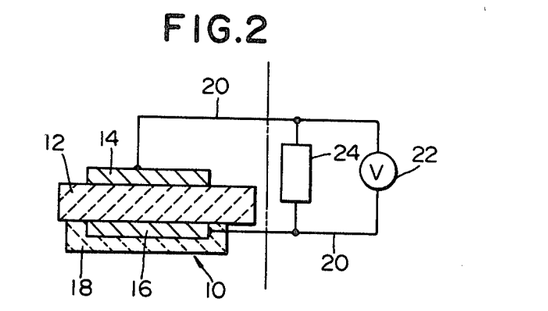
FIG. 2 is a schematic and sectional view of an oxygen concentration measurement apparatus as an embodiment of the invention.

FIGS. 2-5 illustrate practical embodiments of the invention. In FIG. 2, the probe 10 of the oxygen concentration measurement apparatus is constructed by utilizing the solid electrolyte layer 12 as a substrate. In other words, the solid electrolyte layer 12 takes the form of a plate having a thickness sufficient for physical strength of the probe 10. The porous measurement electrode layer 14 is formed, for example, by applying a paste comprising a platinum powder onto one side of the solid electrolyte plate 12 and baking the paste coated plate 12. The porous reference electrode layer 16 is formed on the other side of the solid electrolyte plate 12 by the same method and simultaneously with the measurement electrode layer 14. As in conventional oxygen sensors, the electrode layers 14 and 16 are thinner than the solid electrolyte plate 12. The separation layer 18 in this probe 10 is a porous coating (permeable to oxygen gas) formed on one side of the solid electrolyte plate 12 so as to cover the reference electrode layer 16 entirely and intimately, so that the reference electrode layer 16 communicates with an exterior gas atmosphere only through pores in the separation layer 18. The leads 20 connect the two electrode layers 14 and 16 to the potentiometer 22 and the DC power source 24 in the manner as described hereinbefore. The apparatus of FIG. 2 operates similarly to the apparatus of FIG. 1.

Figure 3:
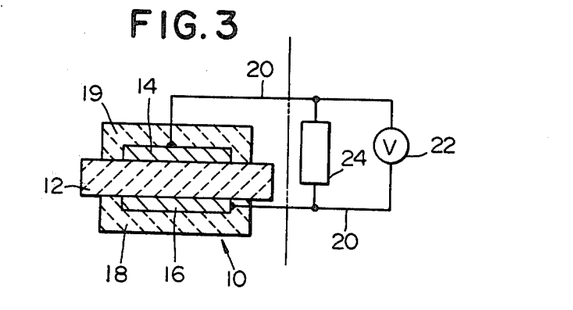
FIG. 3 shows a slight modification of the apparatus of FIG. 2.

Referring to FIG. 3, the measurement electrode layer 14 in the probe 10 of FIG. 2 may optionally be coated with a porous (permeable to oxygen gas) protective coating 19. For example, the protective layer 19 is made of calcium zirconate (CaO—$ZrO_2$ system), alumina or spinel and can be formed by wetting the measurement electrode layer 14 with an aqueous dispersion of such an oxide material and baking the wetted article, or by plasma spraying of the oxide material. Also optionally, the probe 10 of FIG. 1 may entirely be coated with a porous protective layer analogous to the coating 19 in FIG. 3.

Figure 4:
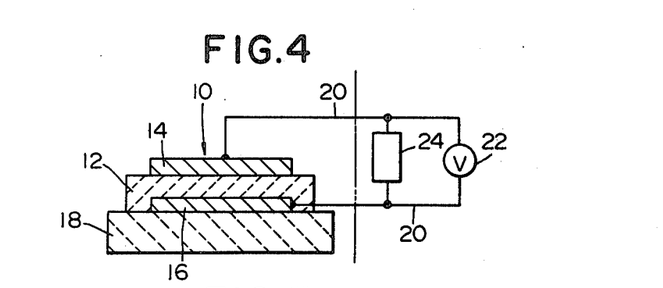
FIG. 4 is a schematic and sectional view of another embodiment of the invention.

In FIG. 4, the separation layer 18 takes the form of a plate thick enough to serve as a substrate of the probe 10. The porous reference electrode layer 16 is formed on one side of the separation layer 18, for example, by the use of a platinum paste. Then the same side of the separation layer 18 is coated with the solid electrolyte layer 12, which is made to have a porous structure in this case, such that the reference electrode layer 16 is entirely coated with the solid electrolyte layer 12. The porous measurement electrode layer 14 is formed on the outer side of the solid electrolyte layer 12. In this case, the solid electrolyte layer 12 may be a thin film formed by sputtering or vacuum evaporation. It will be understood that in principle the function of the probe 10 of FIG. 4 does not differ from that of the probe of FIG. 2.

Figure 5:
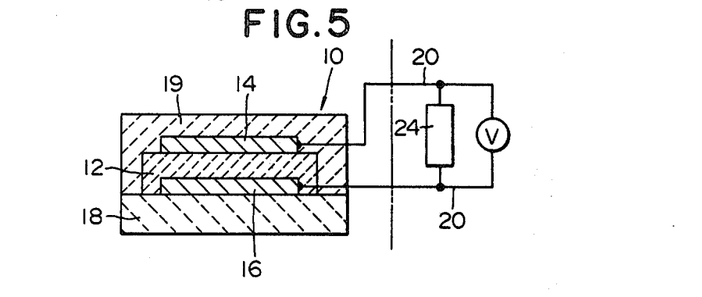
FIG. 5 shows a slight modification of the apparatus of FIG. 4.

FIG. 5 shows that the measurement electrode layer 14 in the probe 10 of FIG. 4 may optionally be coated with the porous protective coating 19 described hereinbefore with reference to FIG. 3 and that the protective coating 19 may be formed so as to cover the solid electrolyte layer 12, too.

The DC power source 24 in an apparatus according to the invention can be selected from conventional constant voltage DC power supply means and constant current DC power supply means. The simplest and most inexpensive embodiment of the DC power source 24 is a combination of a battery and a resistor. However, this embodiment is rather unsatisfactory when the object of measurement is an atmosphere which is liable to exhibit considerable changes in its temperature and/or chemical composition during measurement as exemplified by exhaust gas from an automotive internal combustion engine. Since such changes in the atmosphere subject to measurement cause changes in the internal resistance of the solid electrolyte layer 12, it is impossible to maintain the reference oxygen partial pressure Po(II) at a constant magnitude irrespective of the temperature of the exterior atmosphere by using a simple combination of a battery and a resistor as the DC power source 24. To avoid influences of changes in the temperature and other conditions of the exterior atmosphere on the accuracy of the measurement, it is preferable that the DC power supply 24 in an apparatus according to the invention is a constant current DC power supply circuit. When it is also taken into consideration that changes in temperature of an exterior atmosphere will possibly cause changes in the pore size of the solid electrolyte layer and/or the separation layer 18 and, as a consequence, the rate of inflow or outflow of oxygen gas therethrough, it is most preferable to use a constant current DC power supply circuit including a temperature compensation circuit with a view to further improvement of the accuracy of measurement.

The invention will be further illustrated by the following examples.

EXAMPLE 1

As a solid electrolyte material, use was made of a densely sintered body of $ZrO_2$—$Y_2O_3$ system (9:1 mole ratio). To produce a probe having the construction of FIG. 3, a $10 \times 12$ mm wide and 0.15 mm thick plate was cut out of the sintered solid electrolyte body as the substrate 12 of the probe. A platinum paste (dispersion of finely powdered platinum in an organic medium) was applied onto both sides of the solid electrolyte plate 12, and, after air drying of the applied paste, the plate 12 was baked in air for 1 hr at a temperature of 1300° C., whereby the measurement and reference electrode layers 14 and 16 were formed each in the form of a 1-2 μm thick film. After cooling to room temperature, platinum wires 0.2 mm in diameter were attached to the respective electrode films 14 and 16 by a solderless bonding technique to provide the leads 20. Then, one (16) of the two electrode films was coated entirely with a paste of a glass composition, followed by baking of the plate 12 at 1100° C. for 1 hr, with the result that a porous glass layer was formed as the separation layer 18. Thereafter, calcium zirconate was plasma-sprayed onto the other electrode film 14 to form the porous protective coating 19.

A combination of a battery and a resistor was used as the DC power source 24, and the voltmeter 22 was connected to the probe 10 in the way as illustrated by FIG. 3.

The output characteristic of the thus produced apparatus was examined by the use of a first sample gas whose composition was analogous to an exhaust gas from an automotive internal combustion engine operated with an air-gasoline mixture of which air-to-fuel ratio is about 13, i.e. below a stoichiometric ratio 14.75, and a second sample gas analogous to an exhaust gas from the same engine operated with an air-gasoline mixture whose air-to-fuel ratio is about 16, i.e. above the stoichiometric ratio. It will be understood that the oxygen partial pressure in the first sample gas was far lower than that in the second sample gas. The probe 10 of the apparatus was disposed in a duct, and the two kinds of sample gases were passed through this duct alternately, maintaining the gas temperature at about 600° C. The output voltage of the battery in the DC power source 24 was 4 V, the resistance of the resistor in the power source 24 was 1 MΩ, and the internal impedance of the voltmeter 22 was 10 MΩ.

Figure 6:
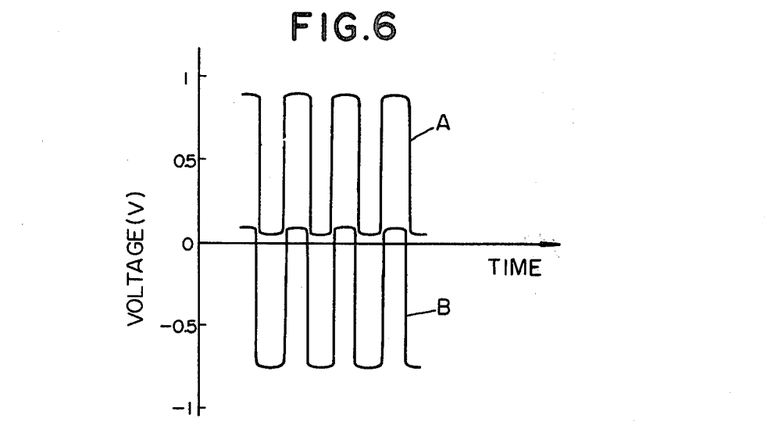
FIGS. 6 and 7 are graphs showing the output characteristics of the apparatus of FIG. 3.

FIG. 6 shows the result of this experiment. The curve A represents the manner of variation in the voltage V detected by the voltmeter 22 when the reference electrode layer 16 was connected to the positive terminal of the battery (24), and the curve B represents the same when the measurement electrode layer 14 was connected to the positive terminal of the battery (24). These curves A and B demonstrate exceedingly sharp and quick responsiveness of an apparatus according to the invention to a change in oxygen partial pressure of a gas subject to measurement. Conventional oxygen sensors of the solid electrolyte concentration cell type exhibit dulling of a time-output curve at each inflection point which appears in response to a sudden and great change in oxygen partial pressure of a sample gas. In contrast, every inflection point on the curves A and B of FIG. 6 is very sharp and can be regarded as being practically free of dulling. As explained hereinbefore and will be understood from a comparison between the curves A and B, a higher level of reference oxygen partial pressure was maintained when the reference electrode layer 16 was connected to the positive terminal of the DC power source 24.

Figure 7:
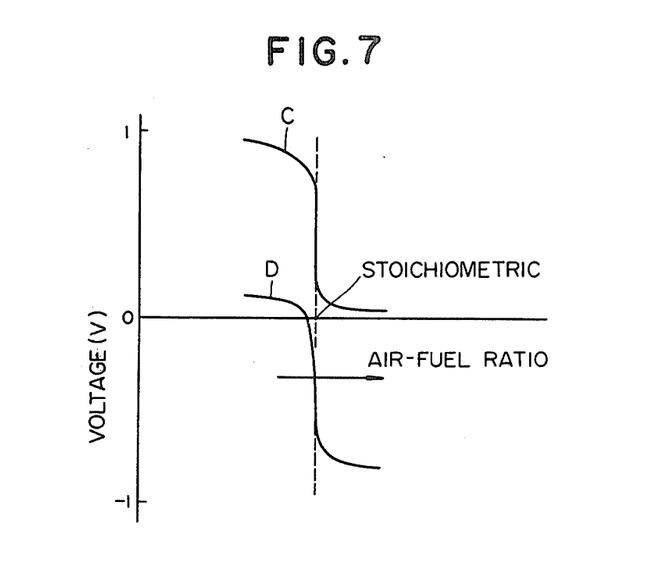

Another experiment was carried out on the performance of the apparatus produced in Example 1. The probe 10 was disposed in an exhaust passage of an automotive internal combustion engine, and the air-to-fuel ratio of an air-gasoline mixture with which the engine was operated was varied continuously. The engine was operated such that the exhaust gas temperature at the location of the probe 10 was constantly about 640° C. FIG. 7 shows the result of this experiment. The curve C was obtained when the reference electrode layer 16 of the probe 10 was connected to the positive terminal of the battery (24) and the curve D when the reference electrode layer 16 was connected to the negative terminal of the battery.

EXAMPLE 2

Figure 8:
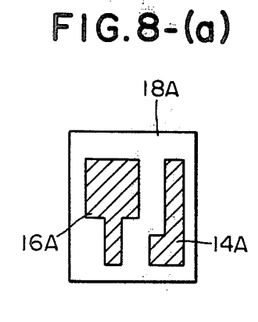

In this example a probe fundamentally of the construction of FIG. 4 was produced by the use of a commercially available 0.6 mm thick alumina plate as the material of the separation layer 18 in FIG. 4. Referring to FIG. 8-(a), this alumina plate was cut into a 10×12 mm piece 18A, and a reference electrode layer 16A was formed on this alumina plate or substrate 18A to a thickness of about 1–2 μm by the employment of the material and method in Example 1. Similarly and simultaneously, a measurement electrode film 14A was formed on the same side of the substrate 18A. As illustrated, the two electrode films 14A and 16A were completely spaced from each other. Then a commercially avaiable paste composed of one part by weight of finely powdered $ZrO_2$—$Y_2O_3$ system (92:8 by weight) and one part by weight of an organic medium was applied onto a major portion of the reference electrode film 16A as indicated at 12A in FIG. 8-(b) by the employment of a screen-printing technique. After air drying of the applied paste 12A, the coated substrate 18A was baked in air for 3 hr at a temperature of 1380° C. As a result, the paste 12A turned into a porous, 30–35 μm thick film of solid electrolyte. Referring to FIG. 8-(c), the aforementioned platinum paste was applied onto the solid electrolyte film 12A as indicated at 14B so as to spread out to the measurement electrode film 14A and cover a narrow region of this electrode film 14A. The platinum paste 14B was converted into a porous platinum film by a heat treatment at 1300° C. for 1 hr, so that the solid electrolyte film 12A was electrically connected to the measurement electrode film 14A by the platinum film 14B.

Using the thus produced probe, an apparatus according to the invention was assembled in accordance with Example 1 and tested in the engine exhaust passage in the manner as described in Example 1. The relationship between the air-to-fuel ratio for operation of the engine and the output of this apparatus was identical with the test result shown in FIG. 7.

The probe produced in Example 2 was subjected to an endurance test in an exhaust passage of an automotive internal combustion engine. The test was made on ten sample probes and continued for a period of time corresponding to the travel of an automobile over a distance of 30000 km, but none of the ten probes exhibited any appreciable change in its output characteristic. For comparison, the same test was made on ten samples of a conventional oxygen sensor comprising a Ni—NiO layer on one side of a solid electrolyte layer. After the endurance test of 30,000 km, it was found that eight of the tested ten samples had become defective.

Figure 10:
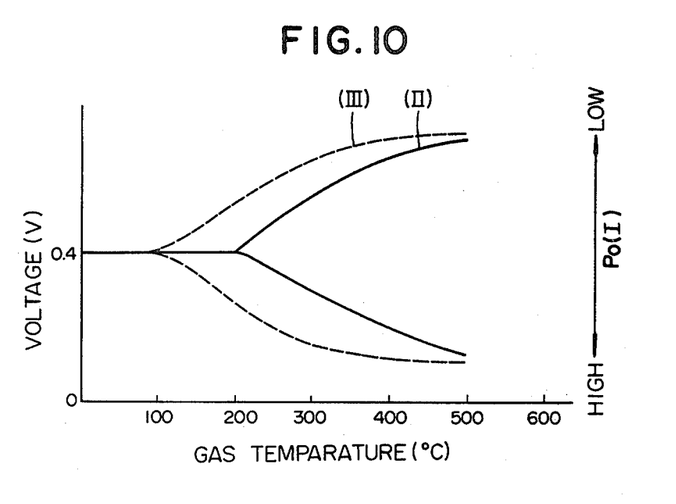
FIG. 10 is a graph showing the output characteristics of measurement apparatus having a probe portion fundamentally constructed as shown in FIG. 9.

Furthermore, the apparatus produced in Example 2 was subjected to the following test to examine temperature dependence of its output voltage. The terminal voltage of the battery (24) was 0.8 V, the resistance of the current feed circuit was 1 MΩ and the impedance of the voltmeter 22 was 1 MΩ. The probe of the apparatus was disposed in an exhaust passage of an automotive internal combustion engine. The air-to-fuel ratio of an air-gasoline mixture fed to the engine was continuously varied within the range between about 13 (low oxygen partial pressure in the exhaust gas) and about 17 (high oxygen partial pressure in the exhaust gas), and the engine was operated so as to vary the exhaust gas temperature at the location of the probe. In FIG. 10, the curve (II) represents the result of this test and demonstrates that an apparatus according to the invention can generate a relatively high output voltage even when used in a considerably low temperature exhaust gas.

This test was repeated except that the battery (24) was replaced by a constant current DC power supply to maintain a constant current of 0.5 μA through the solid electrolyte film 12A between the two electrode films 14A and 16A. As a result, the reference oxygen partial pressure developed in the probe became more stable, and the output characteristic as represented by the curve (II) of FIG. 10 exhibited further improved reproducibility.

EXAMPLE 3

Figure 9:
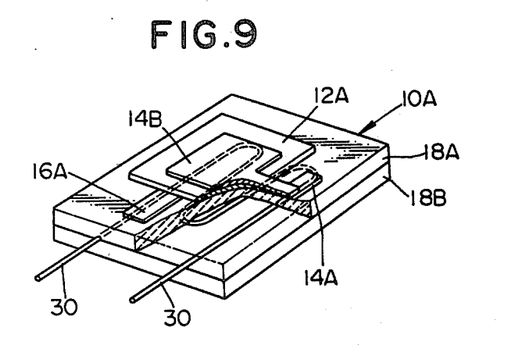
FIG. 9 is a partly cutaway perspective view of a probe which is produced through the steps of FIGS. 8-(*a*) to 8-(*c*) but comprises a heating resistor as an additional element.

A probe 10A as shown in FIG. 9 was produced in this Example. This probe 10A was fundamentally similar to the probe produced in Example 2, i.e. one produced through the steps of FIGS. 8-(a) to 8-(c). As a modification, the substrate of this probe 10A was made up of two alumina plates 18A and 18B bonded together, and a platinum wire 30 was embedded in the substrate to extend on the interface between the two alumina plates 18A, 18B. The resistance of the platinum wire 30 was 1 Ω, and the wire 30 was connected to a power source (not shown) to serve as a heater of 3 W.

An apparatus comprising this probe 10A was subjected to the temperature dependence test described in Example 2 with continued application of a current through the heater wire 30 thereby to keep the probe 10A in a sufficiently heated state. In FIG. 10, the curve (III) represents the result of this test and shows that the provision of the heater 30 to the probe brought about an enlargement of a temperature range in which the probe is satisfactorily operative, that is, the probe became useful even in a very low temperature exhaust gas. Of course the material of the heater wire 30 is not limited to platinum. A few examples of other useful metals are tungsten and molybdenum.

What is claimed is:

1. An apparatus for measurement of oxygen concentration in a fluid, comprising:

a probe comprising a layer of an oxygen ion conductive solid electrolyte, a porous and electronically conductive reference electrode layer formed on and in intimate contact with one side of the solid electrolyte layer, a porous and electronically conductive measurement electrode layer formed on and in intimate contact with the other side of said solid electrolyte layer and a separation layer of an electrochemically inactive material formed on and in intimate contact with the outer side of said reference electrode layer, at least one of said solid electrolyte layer and said separation layer having a porous structure permeable to fluids and being formed such that said reference electrode layer communicates with an exterior atmosphere only through said porous structure, one of said solid electrolyte layer and said separation layer being so shaped and sized as to serve as a structurally basic member of said probe;

a meter connected to said reference electrode layer and said measurement electrode layer for measuring an electromotive force generated by said probe; and a DC power source connected to said reference electrode layer and said measurement electrode layer to continuously apply a DC voltage across said solid electrolyte layer thereby to maintain a reference oxygen partial pressure at the interface between said solid electrolyte layer and said reference electrode layer.

2. An apparatus according to claim 1, wherein said DC power source is a constant current DC power supply.

3. An apparatus according to claims 1 or 2, wherein said reference electrode layer is connected to the positive terminal of said DC power source.

4. An apparatus according to claims 1 or 2, wherein said reference electrode layer is connected to the negative terminal of said DC power source.

5. An apparatus according to claim 1, wherein said solid electrolyte layer takes the form of a plate to serve as said structurally basic member, said separation layer being a porous layer which covers the entire outer surfaces of said reference electrode layer.

6. An apparatus according to claim 1, wherein said separation layer takes the form of a plate to serve as said structurally basic member, said solid electrolyte layer being a porous layer which covers the entire outer surfaces of said reference electrode layer.

7. An apparatus according to claim 6, further comprising a heating resistor embedded in said separation layer.

8. An apparatus according to claim 1, wherein said separation layer is made of an electrically nonconductive inorganic material.

9. An apparatus according to claim 8, wherein said inorganic material is selected from the group consisting of alumina, silica, spinel, mullite and forsterite.

10. An apparatus according to claim 1, wherein said separation layer is made of a metal.

11. An apparatus according to claim 1, further comprising a porous protective layer of an electrochemically inactive material formed on and in intimate contact with outer surfaces of said measurement electrode layer.

* * * * *